United States Patent [19]

Caspers

[11] Patent Number: 5,534,034
[45] Date of Patent: * Jul. 9, 1996

[54] PROSTHETIC POLYURETHANE LINER AND SLEEVE FOR AMPUTEES

[76] Inventor: Carl A. Caspers, 510-8 25th Ave. North, St. Cloud, Minn. 56301

[*] Notice: The portion of the term of this patent subsequent to Nov. 2, 2010, has been disclaimed.

[21] Appl. No.: 146,600

[22] Filed: Nov. 1, 1993

Related U.S. Application Data

[63] Continuation-in-part of Ser. No. 959,523, Oct. 13, 1992, Pat. No. 5,258,037, which is a continuation of Ser. No. 552,445, Jul. 13, 1990, abandoned.

[51] Int. Cl.⁶ .................................................. A61F 2/78
[52] U.S. Cl. ............................. 623/32; 623/34; 623/57
[58] Field of Search ........................... 623/32–37, 57

[56] References Cited

U.S. PATENT DOCUMENTS

| | | |
|---|---|---|
| 2,606,325 | 8/1952 | Nielson et al. . |
| 2,671,225 | 3/1954 | Schoene et al. . |
| 2,696,011 | 12/1954 | Galdik ................................. 623/33 |
| 3,253,600 | 5/1966 | Scholl . |
| 3,322,873 | 5/1967 | Hitchcock . |
| 3,377,416 | 4/1968 | Kandel . |
| 3,732,578 | 5/1973 | Pollack . |
| 3,751,733 | 8/1973 | Fletcher et al. . |
| 3,858,379 | 1/1975 | Graves et al. . |
| 3,895,405 | 7/1975 | Edwards . |
| 3,975,350 | 8/1976 | Hudgin et al. . |
| 3,991,424 | 11/1976 | Prahl . |
| 4,381,768 | 5/1983 | Erichsen et al. ..................... 602/16 |
| 4,466,936 | 8/1984 | Schapel ............................... 264/225 |
| 4,479,272 | 10/1984 | Belzidsky ............................ 623/32 |
| 4,623,354 | 11/1986 | Childress et al. ................... 623/25 |
| 4,634,446 | 1/1987 | Kristinsson ......................... 623/33 |
| 4,635,626 | 1/1987 | Lerman . |
| 4,704,129 | 11/1987 | Massey ............................... 623/25 |
| 4,822,371 | 4/1989 | Jolly et al. .......................... 623/32 |
| 4,828,325 | 5/1989 | Brooks ............................... 297/458 |
| 4,888,829 | 12/1989 | Kleinerman ........................ 2/167 |
| 4,908,037 | 3/1990 | Ross ................................... 623/32 |
| 4,923,475 | 5/1990 | Gosthnian et al. ................. 623/37 |
| 5,007,937 | 4/1991 | Fishman et al. ................... 623/34 |
| 5,133,776 | 7/1992 | Crowder ............................ 623/37 |
| 5,221,222 | 6/1993 | Townes .............................. 2/59 X |
| 5,258,037 | 11/1993 | Caspers ............................. 623/36 |
| 5,314,497 | 5/1994 | Fay et al. ........................... 623/34 |

FOREIGN PATENT DOCUMENTS

| | | | |
|---|---|---|---|
| 0073157 | 9/1960 | France ................................ 623/36 |
| 2712342 | 9/1977 | Germany ........................... 623/35 |
| 1771722 | 10/1992 | U.S.S.R. ............................ 623/57 |

*Primary Examiner*—David H. Willse
*Attorney, Agent, or Firm*—Palmatier, Sjoquist & Helget

[57] ABSTRACT

A visco-elastic polymer liner and sleeve for prosthetic devices utilize the liner for donning over a residual limb and fitting within the socket of an artificial limb. The sleeve is rolled on over the top of the artificial limb and onto the amputee's remaining stump. The liner is shaped to have its cavity formed with a volume and shape less than a volume and shape of the residual limb for both tension and tissue configuration relief while the liner has an outer surface formed with a volume and shape greater than the volume and shape of the artificial limb socket for relief of certain tissue configurations and to create weight bearing, relief and compression areas on and in the liner to absorb and dissipate shock, shear and mechanical forces through the liner otherwise transmitted to the residual limb. The sleeve is shaped like a tube.

22 Claims, 8 Drawing Sheets

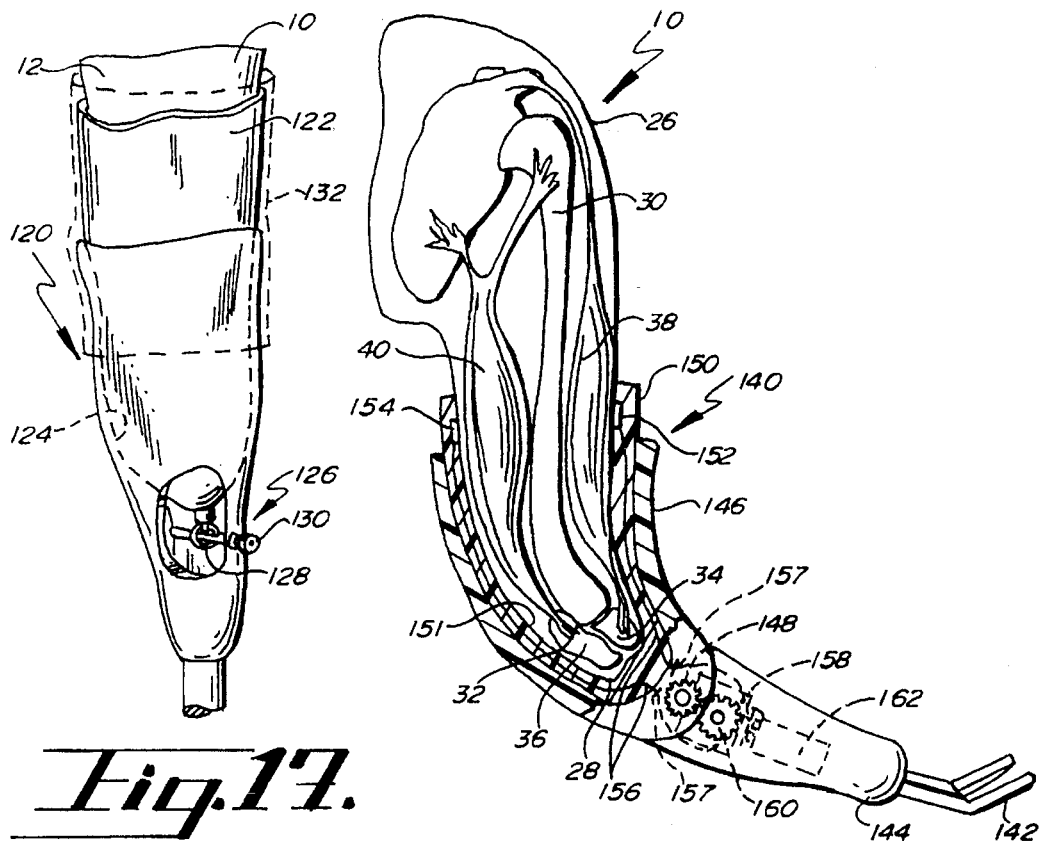
Fig. 17.
Fig. 18.
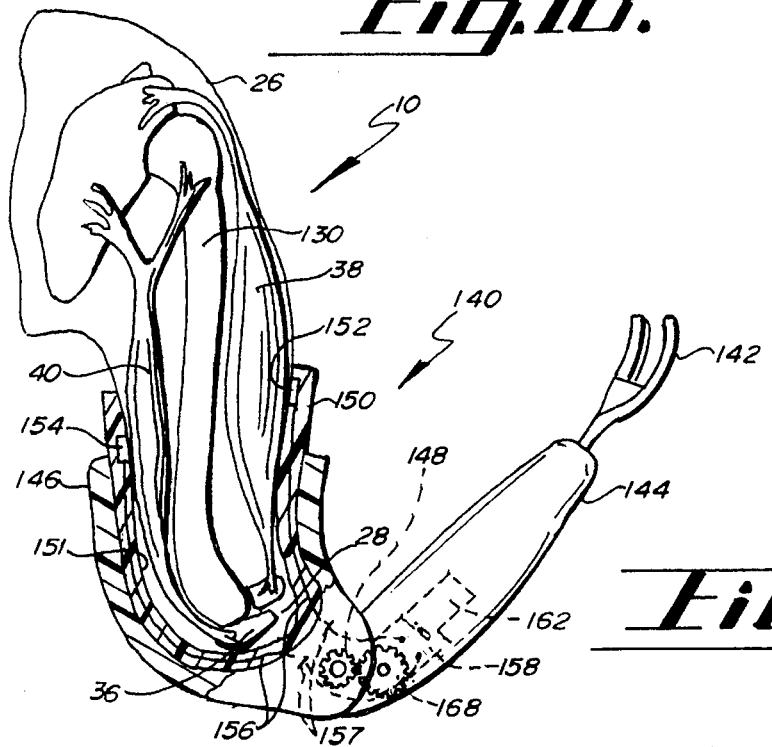
Fig. 19.

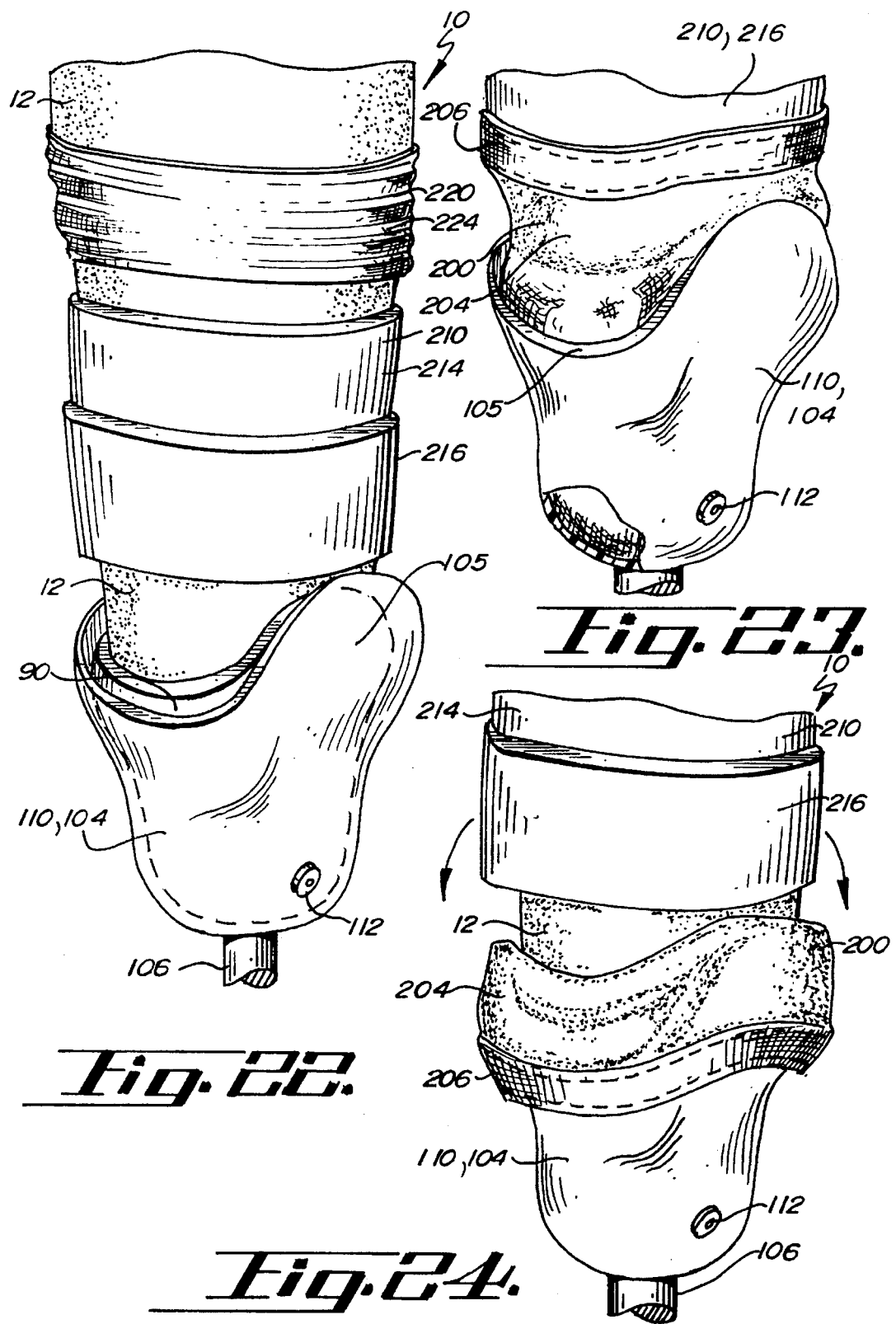

PROSTHETIC POLYURETHANE LINER AND SLEEVE FOR AMPUTEES

This application is a continuation-in-part U.S. application Ser. No. 07/959,523 filed on Oct. 13, 1992, issued on Nov. 2, 1993 as U.S. Pat. No. 5,258,037 which is a continuation of abandoned U.S. application Ser. No. 07/552,445, filed on Jul. 13, 1990, now abandoned.

BACKGROUND OF THE INVENTION

The present invention relates to prosthetic devices and more particularly to an improved liner and sleeve for prosthetic devices including artificial limbs.

An amputee is a person who has lost part of an extremity or limb such as a leg or arm which commonly may be termed as a residual limb. Residual limbs come in various sizes and shapes with respect to the stump. That is, most new amputations are either slightly bulbous or cylindrical in shape while older amputations that may have had a lot of atrophy are generally more conical in shape. Residual limbs may further be characterized by their various individual problems or configurations including the volume and shape of a stump and possible scar, skin graft, bony prominence, uneven limb volume, neuroma, pain, edema or soft tissue configurations.

Referring to FIGS. 1 and 2, a below the knee residual limb 10 is shown and described as a leg 12 having been severed below the knee terminating in a stump 14. In this case, the residual limb 10 includes soft tissue as well as the femur 16, knee joint 18, and severed tibia 20 and fibula 22. Along these bone structures surrounded by soft tissue are nerve bundles and vascular routes which must be protected against external pressure to avoid neuromas, numbness and discomfort as well as other kinds of problems. A below the knee residual limb 10 has its stump 14 generally characterized as being a more bony structure while an above the knee residual limb may be characterized as including more soft tissue as well as the vascular routes and nerve bundles.

Referring to FIG. 3, amputees who have lost a part of their arm 26, which terminates in a stump 28 also may be characterized as having vascular routes, nerve bundles as well as soft and bony tissues. The residual limb 10 includes the humerus bone 30 which extends from below the shoulder to the elbow from which the radius 34 and ulna 36 bones may pivotally extend to the point of severance. Along the humerus bone 30 are the biceps muscle 38 and the triceps muscle 40 which still yet may be connected to the radius 34 and the ulna 36, respectively.

In some respects, the residual limb amputee that has a severed arm 26 does not have the pressure bearing considerations for an artificial limb but rather is concerned with having an artificial limb that is articulable to offer functions typical of a full arm, such as bending at the elbow and grasping capabilities. An individual who has a paralyzed limb would also have similar considerations wherein he or she would desire the paralyzed limb to have some degree of mobility and thus functionality.

Historically, artificial limbs typically used by a leg amputee were for the most part all made out of wood such as an Upland Willow. The limbs were hand carved with sockets for receiving the stump 14 of the residual limb 10. Below the socket would be the shin portion with the foot below the shin. These wooden artificial limbs were covered with rawhide which often were painted. The sockets of most wood limbs were hollow as the limbs were typically supported in the artificial limb by the circumferential tissue adjacent the stump 14 rather than at the distal end of the stump 14.

Some artificial limbs in Europe were also made from forged pieces of metal that were hollow. Fiber artificial limbs were also used which were stretched around a mold afterwhich they were permitted to dry and cure. Again, these artificial limbs were hollow and pretty much supported the residual limb about the circumferential tissue adjacent the stump 14.

All of these various artificial limbs have sockets to put the amputee's stump 28 thereinto. There are generally two categories of sockets. There are hard sockets wherein the stump goes right into the socket actually touching the socket wall without any type of liner or stump sock. Another category of sockets is a socket that utilizes a liner or insert. Both categories of sockets typically were opened ended sockets where they had a hollow chamber in the bottom and no portion of the socket touched the distal end of the stump 14. So, the stump was supported about its circumferential sides as it fits against the inside wall of the sockets.

These types of sockets caused a lot of shear force on the stump 14 as well as had pressure or restriction problems on the nerve bundles and vascular flow of fluid by way of the circumferential pressure effect of the socket on the limb. This pressure effect could cause a swelling into the ends of the socket where an amputee may develop severe edema and draining nodules at the end of their stump 14.

With time, prosthetists learned that by filling in the socket's hollow chamber and encouraging a more total contact with the stump and the socket, the swelling and edema problems could be eliminated. However, the problematic tissue configurations, such as bony prominences, required special consideration such as the addition of soft or pliable materials to be put into the socket.

Today, most artificial limbs are constructed from thermoset plastics such as polyester resins, acrylic resins, polypropylenes and polyethylenes, which are perhaps laminated over a nylon stockinette which also may be impregnated by the various resins.

In the past, most artificial limbs were suspended from the amputee's body by some form of pulley, belt or strap suspension often used with various harnesses and perhaps leather lacers or lacings. Another method of suspending artificial limbs is known as the wedge suspension wherein an actual wedge is built into the socket which is more closed at its top opening. The wedge in the socket cups the medial femoral condyle or knuckle at the abductor tubical. Yet another form of suspension is referred to as the shuttle system or a mechanical hookup or linkup wherein a thin suction liner is donned over the stump that has a docking device on the distal end which mechanically links up with its cooperative part in the bottom of the socket chamber. Sleeve suspensions were also used wherein the amputee may use a latex rubber tube which forms into a rubber-like sleeve which would be rolled on over both the top of the artificial limb and onto the amputee's thigh. The sleeve suspensions have been used in combination with other forms of suspensions techniques.

The first artificial limb socket liners were made with molded horsehide leather covered with strips from extruded sheets of rubber glued to the leather as the liner was built up over a positive cast of the residual limb. As before, stump socks typically made of cotton or wool were used with these first liners as well as with the earlier hard sockets.

The next major socket liner was formed from an expanded foam such as polyurethane foam as sold by Durr-Fillauer Medical, Inc. of Chatanooga, Tenn. After a positive cast was made of the residual limb, a cone-like structure of the hard foam plastic was formed and heated. Next, the expanded foam was pulled over the cast of the residual limb in an effort to form it to the limb after which the foam was cooled and its shape was retained over the positive cast. Thereafter, a hard shell socket could be built or laminated over the liner from which a shin and foot of the artificial limb could be attached.

Another type of socket liner was made from a combination of silicone and gauze being sandwiched in between two pieces of leather. However, this type of liner had problems in that it was much too rigid, wouldn't stretch and eventually loosened up and migrated thereby becoming ineffective.

The next group of socket liners were made from the impregnation of a cotton stockinette with silicone resins formed over a positive cast of the residual limb. The problem with these types of liners is that the silicone could not migrate or stretch and was often short lived in that sweat from the residual limb would break down the silicone and create pungent and unsanitary conditions.

Another type of silicone liner without the impregnated stockinette has been utilized to create suction about the residual limb for use in combination with perhaps a shuttle or mechanical link up device with the socket. However, these types of liners offered no yield or cushion and required the wearing of stump socks.

While some of these devices addressed some of the problems associated with prosthetics, none of the artificial limbs, liners and sockets, individually or in combination, offered a prosthesis that presented a total contact relationship with the residual limb; absorbed and dissipated shear, shock and mechanical forces transmitted to the limb tissues by the artificial limb; controlled perspiration of the residual limb; controlled residual limb volume; and, promoted equal weight distribution while having a long life expectancy.

There is a need for a polyurethane liner and sleeve to be used with prosthetic devices that will offer totals contact relationship with the residual limb; provide hypoboric suction suspension with a sticky or tacky surface condition; absorb and dissipate shock, mechanical and shear forces typically associated with ambulation, twisting and turning and weight bearing with an artificial limb; control perspiration; control residual limb volume by way of even weight distribution; and offer relief for the various tissue configurations that plague residual limbs while yet being of long life.

SUMMARY OF THE INVENTION

A visco-elastic polymer liner and sleeve for prosthetic devices utilize the liner for donning over a residual limb and fitting within the socket of an artificial limb. The sleeve is rolled on over the top of the artificial limb and onto the amputee's remaining stump. The liner is shaped to have its cavity formed with a volume and shape less than a volume and shape of the residual limb for both tension and tissue configuration relief while the liner has an outer surface formed with a volume and shape greater than the volume and shape of the artificial limb socket for relief of certain tissue configurations and to create weight bearing, relief and compression areas on and in the liner to absorb and dissipate shock, shear and mechanical forces through the liner otherwise transmitted to the residual limb. The sleeve is shaped like a tube.

A principal object and advantage of the present liner and sleeve is that they provide comfortably extended wear and range of movement and flexibility heretofore not known to actually permit athletic participation.

Another object and advantage of the present invention is that the liner and sleeve are easy to put on and take off unlike prior complex suspension apparatus and techniques.

Another object and advantage of the present invention is that the liner and sleeve are cosmetically attractive and not bulky like prior belts, straps and harnesses.

Yet another object and advantage of the present invention is that the liner and sleeve are durable for long wear and are readily cleanable with soap and water to provide an odor free clean environment for a residual limb or a paralyzed limb.

Other objects and advantages of the present invention will become apparent from a reading and study of the specification, claims and figures.

BRIEF DESCRIPTION OF THE DRAWINGS

FIG. 5 is a front elevational view of a plaster positive model of the residual limb of FIG. 2 made from the mold of FIG. 4;

FIG. 17 is an elevational view of a mechanical link-up, hook-up or interlocking linkage for securing the residual limb liner to an artificial limb;

FIG. 18 is a side elevational view of an amputee's residual limb donning a bionic or articulable limb partially broken away in an extension position;

FIG. 19 is the residual limb and artificial limb of the FIG. 18 in its flexion position;

FIG. 22 is an elevational view of the residual limb donning the rolled up sleeves placed in the liner which is in the socket without the nylon sheath;

FIG. 23 is an elevational view of the residual limb donning a rolled up sleeve with a nylon sheath over the donned liner placed in the socket;

FIG. 24 is an elevational view similar to FIG. 23 with the upper portion rolled down over the socket brim or lip;

DESCRIPTION OF THE PREFERRED EMBODIMENT

Figures 1, 2, 4:
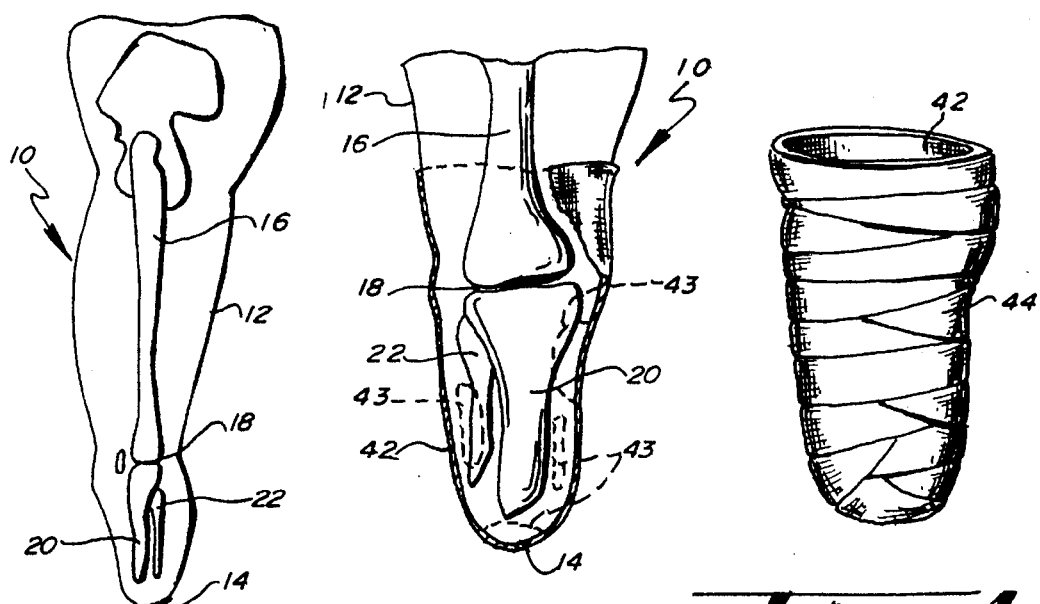
FIG. 1 is a side elevational view of the tissue and skeletal structure of an amputee's residual limb.
FIG. 2 is a front elevational view of a residual limb with a volume and shape and the skeletal structure visible while donning a light cotton marking sock.
FIG. 4 is a front elevational view of a plaster wrap or cast of the residual limb of FIG. 2 constituting a negative model of the residual limb.

Referring to FIGS. 1–5, normally amputees are seen by the prosthetist post operatively after they have had primary wound healing. While the residual limb 12 consists of either a leg 12 or an arm 26, the amputees are evaluated for the size and shape of their stump 14 or 28 with additional considerations given to scar, skin graft, bony prominence, uneven limb volume, neuroma, pain, edema or soft tissue configurations. Through conversations, the amputees are also evaluated as to what their activity levels are.

Next, a single ply thin cotton casting sock 42 is then placed over the residual limb 10. Certain tissue configuration locations as well as pressure sensitive areas are then marked with indelible ink 43 on the casting sock 42. Next an orthopedic plaster wrap 44 that has been dipped in water is formed about the residual limb. After the wrap has been permitted to set and harden, the residual limb 10 is withdrawn from the plaster wrap 44 leaving the casting sock 42 adhered to the plaster wrap. Various separating or releasing media may be used on the residual limb before donning of the casting sock 42, such as a baby powder, vaseline or petroleum jelly, which assists in the removal of the residual limb from the plaster wrap which constitutes the first negative mold of the residual limb 10.

The plaster wrap 44 or first negative mold of the residual limb 10 is next filled with plaster, such as dental plaster, and a centrally located mandrel or pipe 48 is positioned within the plaster cast for later key positioning within a jig or for simply supporting the plaster cast 46 after it is removed from the plaster wrap 46. Again, known separating agents may be used between the plaster wrap 44 and the plaster cast 46.

The plaster cast 46, once removed from the plaster wrap 44, constitutes the original prototype and first positive model 46 of the residual limb 10. As can be seen in the original prototype 46 in FIG. 5, the ink marks 43 readily transfer over to the plaster cast 46 for consideration of the residual limb's volume and shape, category and tissue configurations, such as a scar, skin graft, bony prominence, uneven limb volume, neuroma, edema, pain, pressure sensitive areas and soft tissue. Certain of these areas will require the liner 90 to have varying degrees of thickness and density to accommodate these considerations.

Figures 6, 9:
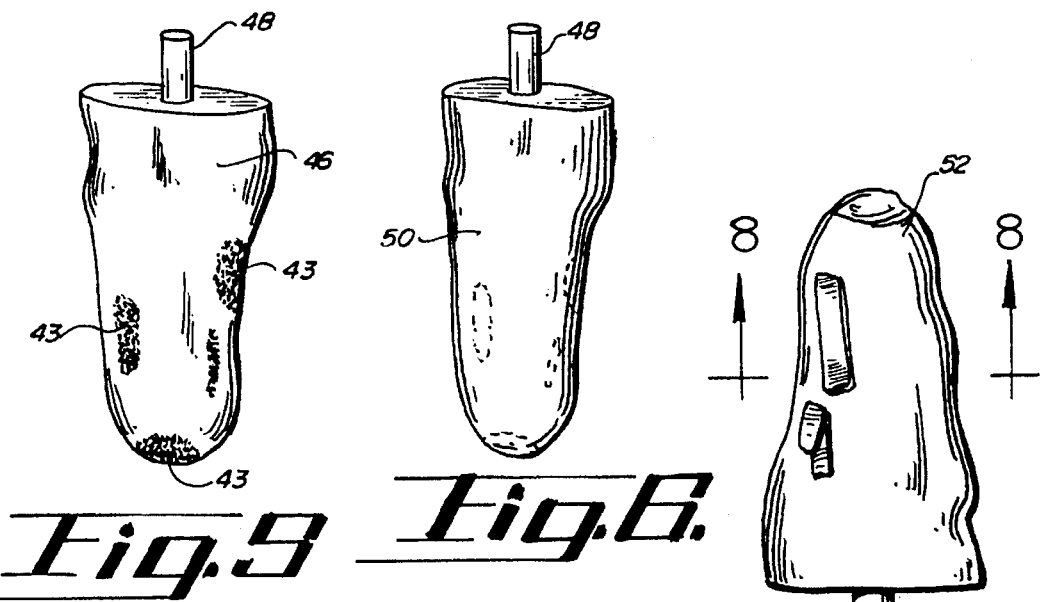
FIG. 6 is a reduced positive model of the residual limb of FIG. 2 formed by reduction of the positive model of FIG. 5 having a volume and shape less than that of the positive model.
FIG. 9 is a front elevational view of the reduced positive model of the residual limb with a second plaster wrap over the filler medium and reduced positive model of the limb as shown in FIG. 7.

Thus, referring to FIG. 6, the original prototype 46 of FIG. 5 is reduced or built up to form the reduced positive model of the residual limb 50. The reduction of this positive model will result in a tension factor on the liner 90 when it is stretched and donned by the residual limb 10, which is a little larger than the volume and shape of the inner cavity 91 of liner 90, as will become clear.

Applicant presently contemplates that computer controlled mills will assist the prosthetists in either shaving off or melting off in a more accurate fashion portions of the original prototype 46 to create the reduced positive model 50 of the residual limb 10.

It is important that the reduced positive model not be reduced in size too much as to create a shear force upon the tissues of the residual limb 10 creating problems.

The prosthetist must next consider what thickness he or she wishes the liner 90 to have. Normally the liner 90 is between five-eights to three-quarters of an inch thick at the stump end 14 and roughly about three-sixteenths to a quarter of an inch thick around the entire residual limb. Additional considerations would include making the liner thinner where specific weight bearing areas of the residual limb would be located as well as making certain areas of the liner 90 thicker to displace and compress the liner 90 in a manner to disperse pressure away from certain tissue configurations. It is also known that where a person is more fleshy, such as in the femur 16 area in the above the knee amputation, the liner 90 would have generally thinner dimensions to add weight bearing areas to the soft tissues. Where there exists a bony prominence, such as in the below the knee amputee, the liner 90 may be a little thicker to disperse the weight bearing areas.

Figures 7, 8:
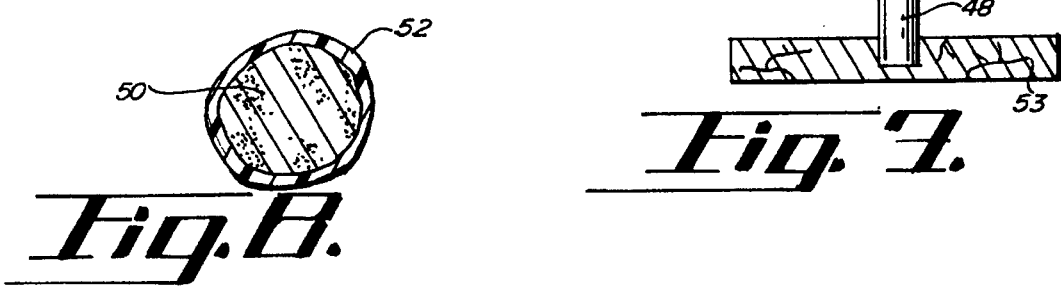
FIG. 7 is a front elevational view of the reduced positive model or prototype of FIG. 6 mounted in a jig with a liner filler medium stretched thereover.
FIG. 8 is a cross-section take along lines 8—8 of FIG. 7.
Figure 9:
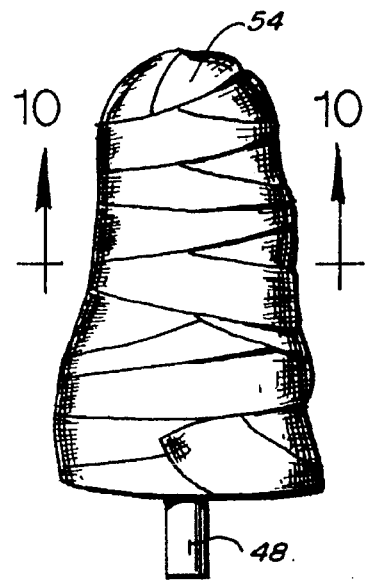

With these considerations in mind, the prosthetist takes the reduced positive model 50 with its mandrel 48 and mounts the model 50 in jig 53 suitably upside down for ease of working as seen in FIG. 7. Thereafter, a filler medium, such as thermoplastic foam 52, is then built on and about the reduced positive model 50 which actually represents the thickness of the liner 90 to be made. The filler medium 52 may be a wool stump sock or various types of expanded thermoplastic foams will also work well. The thermoplastic foams 52 can be readily formed into the shape of a cone and heated. Thereafter, the heated foam 52, which becomes flexible, is formed over the reduced positive model 50 and perhaps vacuumed thereto by way of an evacuated plastic bag being placed over the thermoplastic foam 52. Sheets of the foam 52 that are formed into cone-like structures are available from previously mentioned Durr-Fillauer Medical, Inc. of Tennessee.

As stated, the expanded thermoplastic foam, such as a polyurethane foam or other such expanded foam products such as polyethylene or polypropylene, represents the space where the liner 90 will be. Thus, additional pieces of the foam 52 may be added to the reduced positive model 50, such as the distal end of the stump 14 to form a distal end cap as well as for other areas which may require additional thicknesses due to tissue configurations.

Figure 10:
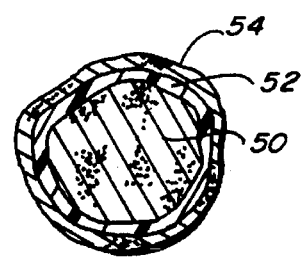
FIG. 10 is a cross sectional view taken along lines 10—10 of FIG. 9.
Figure 3:
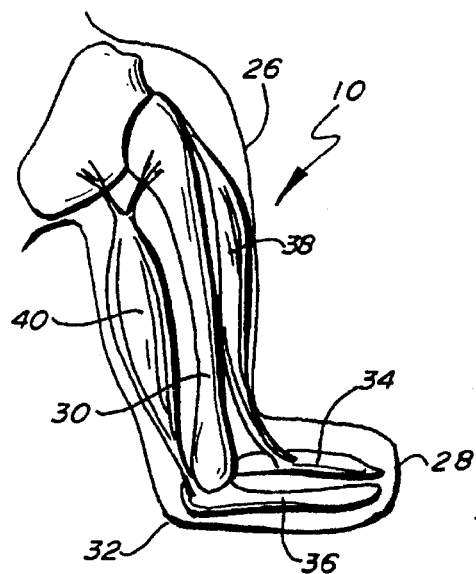
FIG. 3 is a side elevational view of a residual limb in the form of an amputated arm showing the skeletal and muscular structure of the residual limb.

After a releasing or separating medium has been applied to the thermoplastic foam 52, a second plaster wrap 54 is applied over the foam 52 thereby creating a second enlarged negative mold 54 as shown in FIGS. 9 and 10. Thus, the reduced positive model 50 of the residual limb 10 is in a predetermined spaced relationship with the second plaster wrap 54 by way of the thermoplastic foam interface 52.

Figure 11:
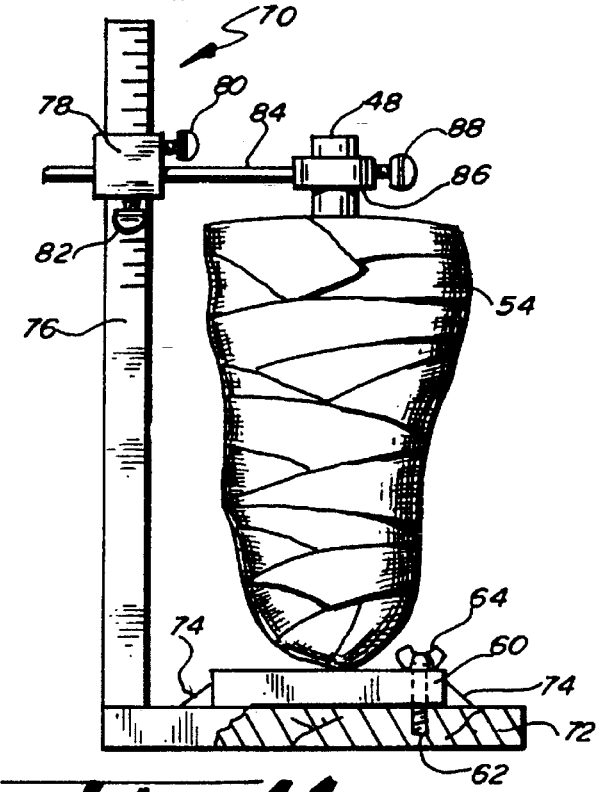
FIG. 11 is an elevational view of the jig for keying the second plaster wrap of FIG. 9 about the reduced positive model of the residual limb of FIG. 6 with the base of the jig partially broken away.
Figure 12:
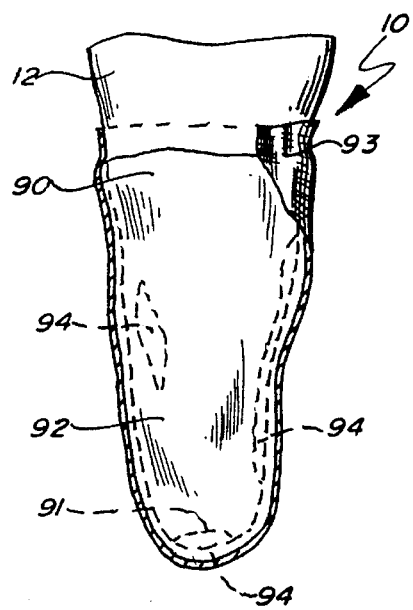
FIG. 12 is a front elevational view of the residual limb donning the liner of the present invention with a light cotton marking sock thereover.
Figure 13:
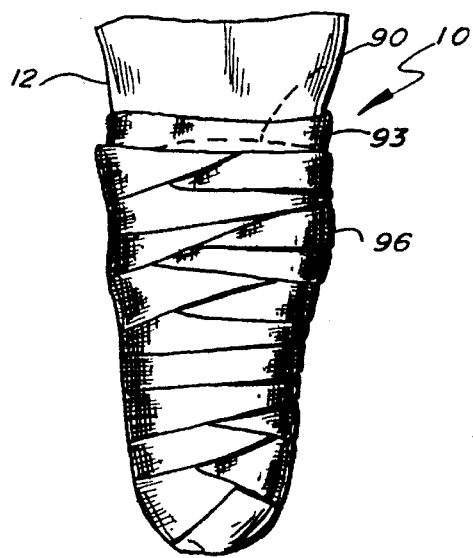
FIG. 13 is a front elevational view of the residual limb with liner and cotton sock of FIG. 12 having a third plaster wrap thereover which is a negative model of the socket.

Referring to FIG. 11, the second plaster wrap 54 has an adaptor block 60, suitably made of wood or foam, affixed to its bottom such as by glue.

The block 60 appropriately has a threaded aperture 62 through which a wing nut screw 64 rotatably may pass. The plaster wrap 54 with its adapter block 6 is now ready for placement within the transfer jig 70. Transfer jig 70, as shown in FIG.7, is a memory device for repeatedly keying the reduced positive model 50 and the second plaster wrap 54 should additional liners 90 be required to be built over time. Transfer jig 70 includes a horizontal plate 72 with keying connectors or ridges 74 which will permit indexing the adaptor block 60 therein for repeated and exact placement of the second plaster wrap 54 upon the transfer jig 70.

Transfer jig 70 also includes a calibrated vertical support 76 having a first collar 78 which adjusts vertically and horizontally and may be secured with respect to those two planes by collar fastener 80. First collar 78 and second collar fastener 82 support, hold and key a horizontal extension 84 which has a second horizontal collar 86 located at its opposing end. The second collar 86 similarly has a collar fastener 88 for locking the collar 86 about mandrel 48.

By this arrangement, reduced positive model 50 of residual limb 10 and the second plaster wrap 54, which is the negative mold of the socket, may be keyed together repeatedly in the exact relationship so that the liner 90 may be repeatedly poured and shaped into the same shape.

With the thermoplastic foam 52 removed from between the reduced positive model 50 and the second plaster wrap 54, the liner 90 in its liquid and moldable form may be introduced into the enlarged negative mold 54. However, the liquid may first be subjected to vacuum, such as in a desiccator, to draw out excess gases and bubbles. Urethane liner 90 is suitably made from a visco-elastic polymer which is energy absorbing and flexible exhibiting a flowability or internal movement character with recovery of shape or memory. Applicant has found that a polyurethane elastomer is suitably appropriate in that it is further washable, durable, bacterial static and fungistatic. Urethanes are technically called a carbamate ester which is made from a combination of isocyanates and alcohols. More definitively, applicant has found that aromatic diisocyanate and elasticizing polyols, such as diols or triols, form suitably nonfoaming, nonporous urethanes or polyurethanes.

Applicant has found that a preferable polyurethane includes the combination of an antioxidant with free toluene diisocyanate and a blend of polyether polyols with bismuth carboxylate. These components are commercially available from Rieckens Orthodics Laboratories of 401 North Green River Road, Evansville, Ind. 47715 and have been used in the past as sole material or inlay for use with shoes. Although energy absorbing polymers have been used as sole or inlays for shoes, they have never been utilized in the context of the present invention or prosthetic.

Applicant has also found that vinyl resins or moldable thermoplastics exhibiting visco-elastic polymer qualities, energy absorption, flexibility, flowability and recovery also will work in forming liner 90.

Once the diiosocyanate and polyols components have been mixed together forming viscous fluid with the appropriate and predetermined durometer, the fluid is poured into the second plaster wrap 54. The reduced positive model 50 of the residual limb 10 is then placed into the second plaster wrap 54 and keyed into the transfer jig 70 as if thermoplastic foam 52 was still interfaced between the model 50 and the wrap 54. A releasing agent, such as a silicone base mold separator, may be utilized between the wrap 54 and the model 50 so that the liner 90 will readily separate after being permitted to set and cure after one or two hours. Separators are also available from Rieckens Orthodics Laboratories.

Referring to FIGS. 12–16, the prosthetist next has the amputee don the urethane liner 90 over his or her residual limb 10 after the urethane liner 90 has been cleaned up and washed with soap. If the polyurethane liner 90 is of extensive length, the amputee may need a wetting agent such as a petroleum jelly which will readily dissipate. Otherwise, the liner 90 is slid or rolled onto the amputee's residual limb 10. Should the liner 90 require some build up, the freshly mixed components will readily adhere to the liner 90.

Thereafter, another single ply thin cotton casting sock 93 is then placed over the liner 90 which is marked with the indelible ink 94 for a second consideration of certain previously mentioned tissue configurations such as bony prominences, pressure areas and scar problems. This step is necessary because once the liner 90 is donned over the residual limb 10 with some degree of tension, some of the relief, shape and volume adjustments previously made become dissipated.

Thereafter, a third plaster wrap 96 or a negative model of the artificial limb socket 104 is then made about the residual limb 10 with the liner 90 and marked up casting sock 93 thereon.

Figure 14:
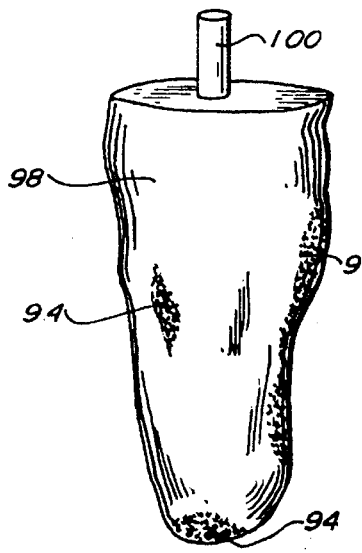
FIG. 14 is a plaster cast or positive model of the socket made from the plaster wrap of FIG. 13.
Figure 15:
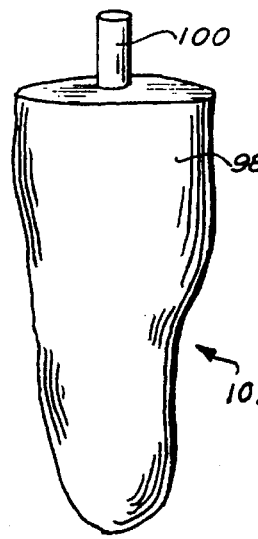
FIG. 15 is a reduced positive model of the socket made from the model of FIG. 14 having a volume and shape less than that of the positive model of FIG. 14.

After the third plaster wrap 96 has cured and the residual limb 10, liner 90 have been removed from the third plaster wrap 96 or negative model of the socket, a plaster cast or positive model of the socket 98 is made from dental plaster. Suitably a mandrel 100 is placed in the plaster 98 to assist in construction of the socket 104. As seen in FIG. 14, a positive model of the socket 98 has the ink marks 94 for certain reduction and build up considerations for various tissue configurations and so on.

Next, the positive model of the socket 98 is milled or shaved to create a reduced positive model of the socket 104 which is necessary to create weight bearing areas and compression upon the liner against the inner cavity 91 of the liner 90 on the residual limb and upon the outer surface 92 of the liner 90 upon the socket 104.

Figure 16:
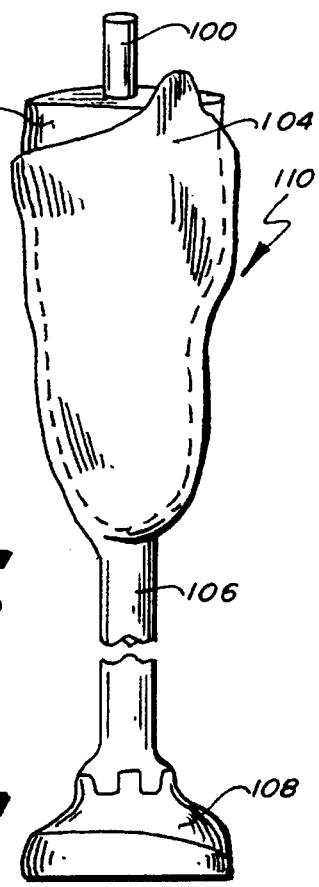
FIG. 16 is a side elevational view of the socket and remaining parts of an artificial limb laminated or built about the reduced positive model socket of FIG. 15.

Referring specifically to FIG. 16, the artificial limb 110 includes its socket 104, shin 106 and foot 108. The limb 110 may be constructed by way of polyester or acrylic resins laminated over nylon stockinettes or by way of thermoset plastics including polypropylene and polyethylene. The artificial limb 110 may use various suspension techniques as mentioned. Once the socket 104 has been formed by lamination over the reduced positive model of the socket 104, the artificial limb 110 is most suitable for total contact hypoboric suction shuttle suspension as shown in FIG. 17. By this arrangement, the liner 122 is donned by the artificial limb and placed within socket 124. A releasably mechanical interlocking hookup or linkage 126 includes a ring 128 supported by a mounting means in the liner and a pin 130 mounted in the socket adjacent the shin. As previously stated, a sleeve 132 may also be placed over the artificial limb 120 and the leg 10.

The visco-elastic, energy absorbing, flexible polymer liner of the present invention has applications beyond that of merely being a total contact hypoboric suction, equal weight distribution socket liner. That is, the polyurethane liner, which readily tacks up to the skin of the human body to the point of almost actually becoming part of the skin, readily permits the proper location of electrodes for use and application of bionic artificial limbs or the application of creating movement of paralyzed limbs.

Referring to FIGS. 18 and 19, the application of the present invention in a bionic artificial limb or arm 140 will be explained. The amputee's arm 26 consists of a stump 28 below the elbow 32 wherein the radius 34 and ulna 36 bones have been severed. The amputee has normal and innervated bicep and tricep muscles 38 and 40 along the humerus with the exception that their lower most connection to the radius and ulna, which have been severed, provide no lever for these muscles to permit a function.

Consequently, a bionic or articulable artificial arm 140, as is known, typically would have a moveable hook or hand 142 and a pivotally mounted motor driven forearm 144 connected to the above elbow socket section 146. The socket section 146 has a pivot gear 148. The polyurethane liner 150 of the present invention includes an inner cavity 151 which has a biceps electrode 152 and a triceps electrode 154. The electrodes 152 and 154 touch the skin and lie over the muscles 38 and 40 in a predetermined location to monitor muscle action potential. The electrodes 152 and 154 are then wired 156 through the liner 150 to touch plates 157 which are further wired into the bionic arm 140. Signals from the electrodes 152 and 154, which sense muscle action potentials, are amplified and relayed to a forearm 144 control motor 158 which operates gear 160, all of which are powered by battery 162.

In operation, the amputee consciously flexes his biceps muscle 38. The muscle action potential is then sensed by bicep electrode 152 after which it is relayed and amplified to engage motor 158 and gear 160 to drive the forearm portion 144 of bionic arm to a flexion motion. When the amputee wishes to have the forearm 144 move into an extension or downward motion, the amputee simply flexes his or her tricep muscles 40. The muscle action potential is then sensed by triceps electrode 154 which similarly engages motor 158 and gear 160 in reverse operation to move the forearm 144 downwardly.

The liner 150 of the present invention permits this operation with repeated accuracy due to the liners construction, location of the electrodes 152 and 154 and wires 157 within the liner by way of forming the liner as previously stated. The exact construction and donning of the liner 150 will assure that electrodes 152 and 154 are repeatedly placed over the proper location on the amputee's skin and wires 156 will engage or touch plates 157.

Figure 20:
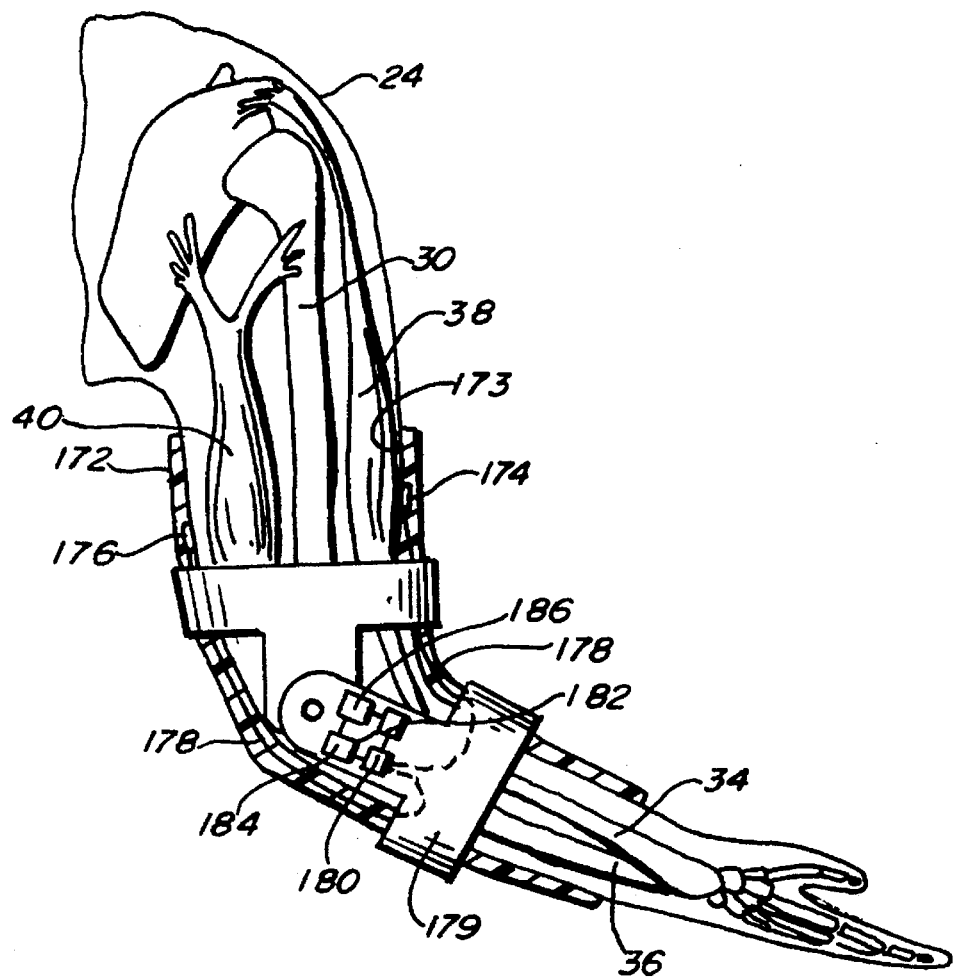
FIG. 20 is an elevational view of a paralyzed upper limb or arm donning a bionic harness for actuating paralyzed muscle movement.
Figure 21:
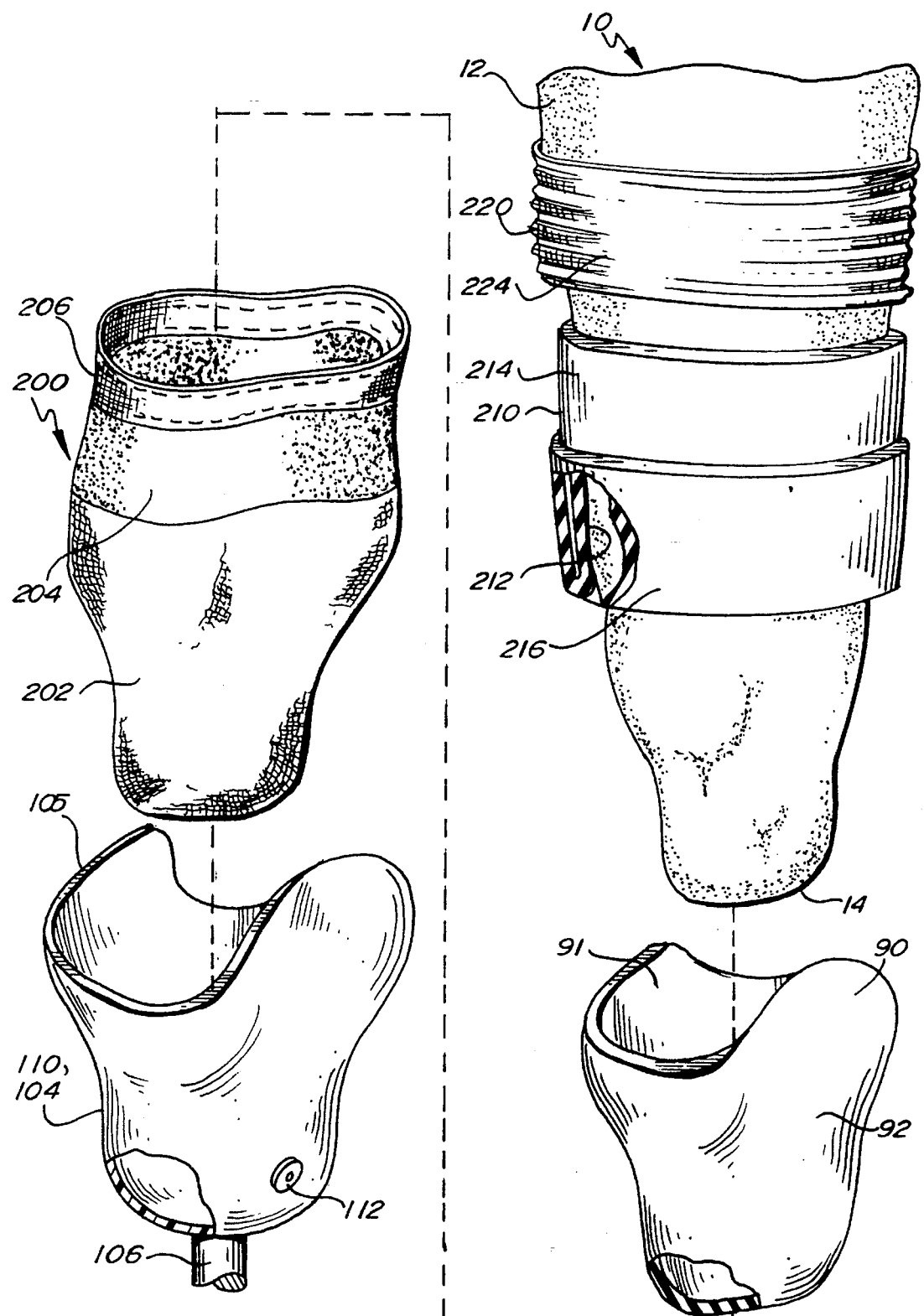
FIG. 21 is an exploded elevational view of the residual limb donning the polyurethane sleeve, stretchable nylon sleeve, polyurethane liner, nylon sheath and socket of an artificial limb.

Referring to FIG. 20, the liner of the present invention has application for individuals who have a paralyzed limb 170 wherein the paralysis is due to a disconnection along the nerve pathways between the brain and the muscle. In other words, the muscles 38 and 40, once properly stimulated, will permit flexion and extension of the paralyzed individuals's forearm.

Initially the proper locations to stimulate the bicep and tricep muscles 38 and 40 must be predetermined by known means, such as a "Tens device." Thereafter, a polyurethane liner or tube 172 is formed as previously disclosed herein having an inner wall 73. The bicep and tricep electrodes and 174 and 176 are then placed within the liner during its formation with connection wires 178. Wires 178 are connected to a bionic harness 179 as shown. The electrodes 174 and 176 are connected by way of the wires 178 to a muscle action potential generator 180 which receives signals from amplifier 184 and limb flexion or extension signal receiver 186, all of which are powered by battery 182. When a flexion or extension signal is received by the receiver 186, a muscle action potential is discharged at the electrodes 174 or 176 likely located near a neuromuscular junction which will initiate either flexion or extension.

Again, it is the unique method of construction and materials from which the present liner is made which permits exact location of electrodes on a repeated basis on an individual's skins together with the tacking up of the liner upon the skin no matter what the individual's position or activity level that permits the liner to be readily applicable to bionics or robotics.

Referring to FIGS. 21–26, the polyurethane tubular sleeve 210 may be appreciated alone and in combination with the urethane liner 90 together with the optional nylon sheath 200 and second stretchable nylon sleeve 220.

More specifically, the amputee takes the stretchable nylon second sleeve 220, suitably made of a spandex-like material, that has an inside 222 and outside 224 and rolls it up over the stump 14 to the upper portions of the residual limb suitably as the thigh of a leg 12. Next, the polyurethane sleeve 210 is also rolled upwardly over the residual limb 10. The sleeve has an inside 212, an outside 214, and a rolled back portion 216. Thereafter, the liner 90 is donned.

Next, the amputee may optionally utilize the nylon sheath 200 which is suitably of a nonstretching, thin, friction reducing nylon. The sheath 200 has a stump with a liner receiving lower portion 202 and a double knit upper portion 204. The upper portion 204 also appropriately may have a stretch band 206 made of rubber elastic or the like. As stated, this sheath 200 optionally may be used to assist the amputee into a smooth and easy fitting into the socket 104 as shown in FIG. 23. Alternatively, the sheath 200 may be avoided and the liner 90 simply inserted into the socket 104 of the artificial limb 110. Optionally, an air valve 112 may be utilized in the socket to allow the ingress and outgress of air as the liner 90 is slid into the socket 104.

When utilizing the sheath as shown in FIG. 23, the sheath may then have its double knitted upper portion 204 rolled downwardly over the socket brim or lip 105 and over a substantial portion of a socket 104 as shown in FIG. 24. The stretch band 206 appropriately secures the sheath 200 in place about the socket 104 of the artificial limb 110. Next, the amputee simply grasps the rolled over portion 216 of the polyurethane sleeve 210 and rolls it over the sheath 200 and over a substantial portion of the socket 104. As can be appreciated, the polyurethane sleeve 210 is tacky. Consequently, the stretchable nylon second sleeve 220 is utilized and rolled over the polyurethane sleeve 210 as shown in FIG. 25.

Figures 25, 26:
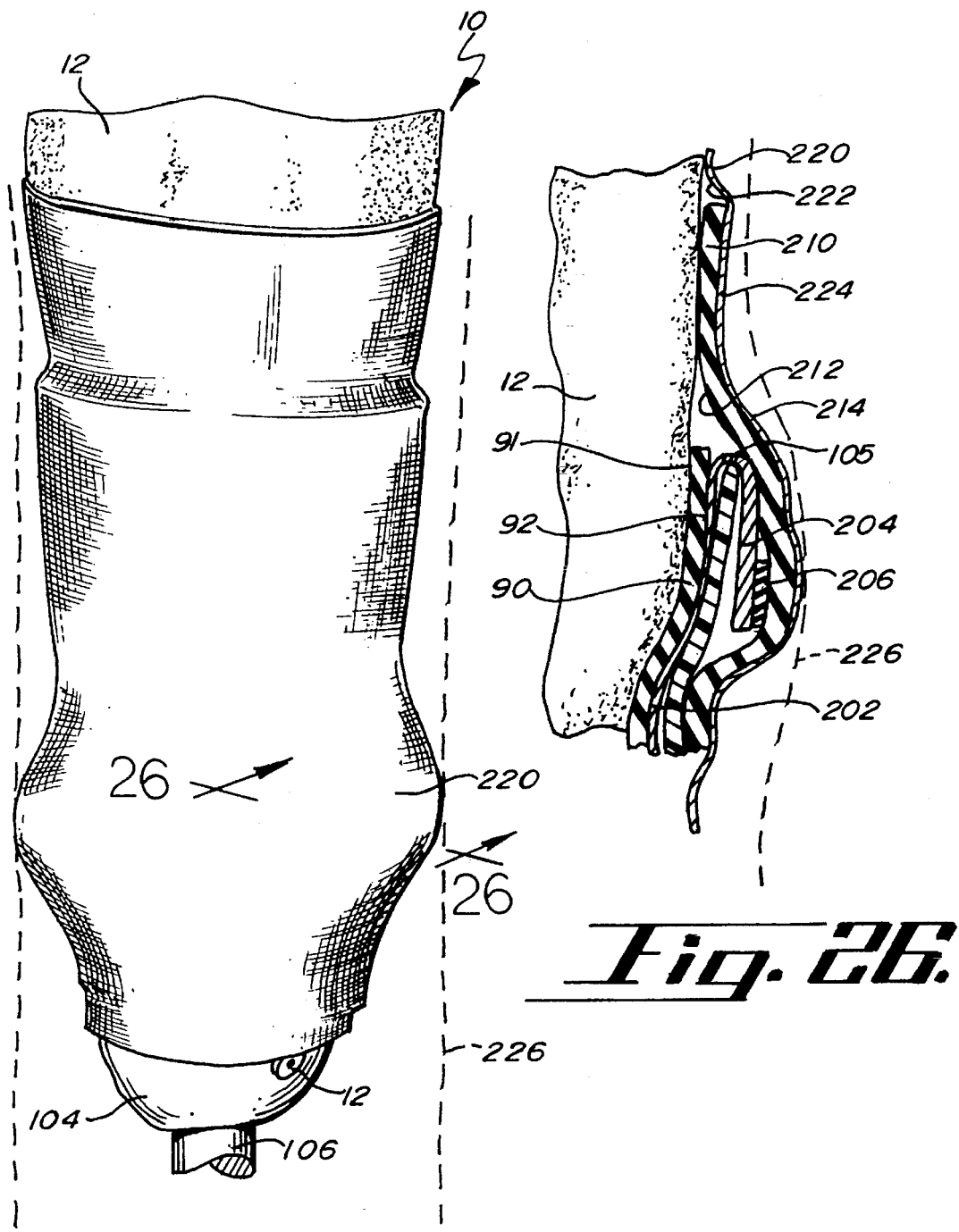
FIG. 25 is an elevational view of the polyurethane sleeve and second stretchable nylon sleeve rolled over the socket and residual limb with clothing shown in broken outline.
FIG. 26 is a broken away partial cross sectional view taken along lines 26—26 of FIG. 25.

FIG. 26 shows a broken away partial cross sectional view of the liner and sleeve arrangement of the present invention. It may be appreciated that the stump of leg 12 is fitted within the inner cavity 91 of liner 90. The outer surface 92 of liner 90 is in contact with the socket 104. The optional sheath 200 covers the liner 90 and is rolled over the socket brim 105 and is held over the outside of socket 104 suitably by the stretch band 206 which also may be a string or the like. Over this assembly is the polyurethane sleeve 210 with its inside 212 tacking up to the residual limb 10 or 12 and the outer portion of the socket 104. The double knit upper portion 204 of the sheath 200 permits the polyurethane sleeve 210 to move about the socket 104 freely as the limb is moved or flexed. Appreciating that the outside 214 of the polyurethane sleeve 210 is also tacky, a stretchable nylon second sleeve 220 is rolled thereover. The second sleeve has its inside 222 confronting the present invention while its smooth outside 224 permits the smooth and free movement of a garment 226 (pants or a dress) from catching or tacking up to the polyurethane sleeve 210.

The present invention may be embodied in other specific forms without departing from the spirit or essential attributes thereof; therefore, the illustrated embodiment should be considered in all respects as illustrative and not restrictive, reference being made to the appended claims rather than to the foregoing description to indicate the scope of the invention.

What is claimed is:

1. A prosthesis for an amputee who has a residual limb, the prosthesis comprising:
   (a) an artificial limb having a socket with a volume and shape to receive a substantial portion of the residual limb with a space therebetween;
   (b) a nonfoamed, nonporous polyurethane liner with a cavity with a volume and shape for receiving a substantial portion of the residual limb and fitting in the space between the socket and the residual limb with the liner donned on the residual limb; and
   (c) a nonfoamed, nonporous polyurethane suspension sleeve open therethrough for rolling over and covering the socket of the artificial limb and a portion of the amputee's residual limb to flexibly secure the residual limb to the artificial limb.

2. The prosthesis of claim 1, wherein the suspension sleeve is a tube.

3. The prosthesis of claim 1, wherein the polyurethane is comprised of predetermined mixed amounts of nonfoaming isocyanates and polyols.

4. The prosthesis of claim 1, further comprising a valve in the socket to release air into and out of the socket when placing and removing the donned liner into the socket.

5. The prosthesis of claim 1, further comprising a thin knitted nylon sheath having a stump and liner receiving portion to aid and reduce friction in placing and removing the donned liner into and from the socket.

6. The prosthesis of claim 5, wherein the sheath has an upper portion to fold downwardly over the socket after the donned liner with sheath is placed in the socket to permit the suspension sleeve to slide about the socket during flexation and movement of the residual and artificial limbs.

7. The prosthesis of claim 6, wherein the upper portion of the sheath is double-knitted.

8. The prosthesis of claim 6, wherein the upper portion of the sheath has a stretch band therearound for securing the sheath down and over the socket.

9. The prosthesis of claim 1, further comprising a stretchable nylon second sleeve for rolling over and covering the suspension sleeve to prevent clothing from sticking to and catching the suspension sleeve.

10. A prosthesis for an amputee who has a residual limb, the prosthesis comprising:
    (a) an artificial limb having a socket with a volume and shape to receive a substantial portion of the residual limb with a space therebetween;
    (b) a nonfoamed, nonporous polyurethane liner with a cavity with a volume and shape for receiving a substantial portion of the residual limb and fitting in the space between the socket and the residual limb with the liner donned on the residual limb;
    (c) a thin knitted nylon sheath having a stump and liner receiving portion to aid and reduce friction in placing and removing the donned liner into and from the socket;
    (d) a nonfoamed, nonporous polyurethane suspension sleeve open therethrough for rolling over and covering the socket of the artificial limb and a portion of the amputee's residual limb to flexibly secure the residual limb to the artificial limb; and
    (e) a stretchable nylon second sleeve open therethrough for rolling over and covering the suspension sleeve to prevent clothing from sticking to and catching the suspension sleeve.

11. The prosthesis of claim 10, wherein the suspension sleeve is a tube.

12. The prosthesis of claim 10, wherein the polyurethane is comprised of predetermined mixed amounts of nonfoaming isocyanates and polyols.

13. The prosthesis of claim 10, further comprising a valve in the socket to release air into and out of the socket when placing and removing the donned liner into the socket.

14. The prosthesis of claim 10, wherein the sheath has an upper portion to fold downwardly over the socket after the donned liner with sheath is placed in the socket to permit the suspension sleeve to slide about,the socket during flexation and movement of the residual and artificial limbs.

15. The prosthesis of claim 14, wherein the upper portion of the sheath is double-knitted.

16. The prosthesis of claim 14, wherein the upper portion of the sheath has a stretch band therearound for securing the sheath down and over the socket.

17. A prosthesis for an amputee who has a residual limb, the prosthesis comprising:
    (a) an artificial limb having a socket with a volume and shape to receive a substantial portion of the residual limb with a space therebetween;
    (b) a nonfoamed, nonporous polyurethane liner with a cavity with a volume and shape for receiving a substantial portion of the residual limb and fitting in the space between the socket and the residual limb with the liner donned on the residual limb;
    (c) a thin knitted nylon sheath having a stump and liner receiving portion to aid and reduce friction in placing and removing the donned liner into and from the socket and an upper portion to fold downwardly over the socket after the donned liner with sheath is placed in the socket to permit a suspension sleeve to slide about the socket during flexation and movement of the residual and artificial limbs;
    (d) the suspension sleeve open therethrough being nonfoamed, nonporous polyurethane and for rolling over and covering the socket of the artificial limb and a portion of the amputee's residual limb to flexibly secure the residual limb to the artificial limb; and
    (e) a stretchable nylon second sleeve open therethrough for rolling over and covering the suspension sleeve to prevent clothing from sticking to and catching the suspension sleeve.

18. The prosthesis of claim 17, wherein the suspension sleeve is a tube.

19. The prosthesis of claim 17, wherein the polyurethane is comprised of predetermined mixed amounts of nonfoaming isocyanates and polyols.

20. The prosthesis of claim 17, further comprising a valve in the socket to release air into and out of the socket when placing and removing the donned liner into the socket.

21. The prosthesis of claim 17, wherein the upper portion of the sheath is double-knitted.

22. The prosthesis of claim 17, wherein the upper portion of the sheath has a stretch band therearound for securing the sheath down and over the socket.

* * * * *

UNITED STATES PATENT AND TRADEMARK OFFICE
CERTIFICATE OF CORRECTION

PATENT NO. : 5,534,034
DATED : July 9, 1996
INVENTOR(S) : Carl A. Caspers

It is certified that error appears in the above-identified patent and that said Letters Patent is hereby corrected as shown below:

Column 3, line 39, please delete the word "hypoboric" and insert in its place --hypobaric--.

Column 3, line 38, please delete the word "totals" and insert in its place --total--.

Column 8, line 55, please delete the word "hypoboric" and insert in its place --hypobaric--.

Column 8, line 66, please delete the word "hypoboric" and insert in its place --hypobaric--.

Signed and Sealed this

Third Day of December, 1996

Attest:

BRUCE LEHMAN

Attesting Officer     Commissioner of Patents and Trademarks